United States Patent [19]
Ansell

[11] Patent Number: 6,027,726
[45] Date of Patent: *Feb. 22, 2000

[54] GLYCOSYLATED PROTEIN-LIPOSOME CONJUGATES AND METHODS FOR THEIR PREPARATION

[75] Inventor: Steven Michial Ansell, Vancouver, Canada

[73] Assignee: Inex Phamaceuticals Corp., Burnaby, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/536,396

[22] Filed: Sep. 29, 1995

Related U.S. Application Data

[63] Continuation-in-part of application No. 08/418,696, Apr. 7, 1995, abandoned, which is a continuation-in-part of application No. 08/316,394, Sep. 30, 1994, abandoned.

[51] Int. Cl.$^7$ .................................................. A61K 39/395
[52] U.S. Cl. ................... 424/180.1; 424/450; 424/179.1; 424/181.1; 530/391.9; 530/391.5; 530/350; 530/395; 530/402
[58] Field of Search ............................. 530/391.9, 391.5, 530/350, 351, 395, 402; 424/450, 179.1, 180.1, 181.1

[56] References Cited

U.S. PATENT DOCUMENTS

| | | | |
|---|---|---|---|
| 5,045,451 | 9/1991 | Lihr et al. | 435/7.23 |
| 5,191,066 | 3/1993 | Bieniarz et al. | 530/391.1 |

OTHER PUBLICATIONS

Seaver, Genetic Engineering News, pp. 10 and 21 (1994).
Harris et al., TIBTECH, vol. 11, pp. 42–44, (1993).
Hermentin et al., Behring Inst. Mitt, No. 82, pp. 197–215 (1988).
Canevari et al, Annals Of Oncology, vol. 5, pp. 698–701, (1994).
Klibanov et al., Journal of Liposome Research vol. 2(3) pp. 321–334 (1992).
Woodle et al., Biochim Biophys Acta, vol. 1105 pp. 193–200 (1992).
Chua et al, Biochimica et Biophysica Acta, 800(1984), 291–300.
Heath, T.D., et al. (1986) "The development and application of protein–liposome conjugation techniques," *Chemistry and Physics of Lipids*, 40:347–358.
Domen, P.L., et al. (1990) "Site directed immobilization of protein," *The Journal of Chromatography*, 510:293–302.
Chua, M.M., et al. (1984) "Attachment of immunoglobulin to liposomal membrane via protein carbohydrate," *Biochimica et Biophysica Acta*, 800:291–300.
Taylor, K.E., et al. (1980) "A thiolation reagent for cell surface carbohydrate," *Biochemistry International*, 1(4):353–358.

(List continued on next page.)

*Primary Examiner*—Keith D. MacMillan
*Assistant Examiner*—T. D. Wessendorf
*Attorney, Agent, or Firm*—Townsend and Townsend and Crew LLP

[57] ABSTRACT

The present invention provides glycosylated protein-liposome compositions which are useful for the targeted delivery of a therapeutic agent. The compositions contain an oxidized protein, typically an antibody, which is covalently attached to a lipid by means of a crosslinking agent having an acid hydrazide functionality on one terminus and a sulfhydryl functionality on the other terminus. The lipid is present in a liposome formulation. Methods for preparing the compositions are also provided. In the methods, a glycosylated protein is first oxidized then reacted with a lining group having an acid hydrazide on one end and a sulfhydryl or protected sulfhydryl group on the other end. The resultant modified protein is then reacted with a liposome formulation of a lipid having a sulfhydryl reactive functional group to covalently attach the protein to the liposome.

4 Claims, 9 Drawing Sheets

OTHER PUBLICATIONS

Bottscher, C.J.F., et al. (1961), A rapid and sensitive sub-micro phosphorus determination *Anal. Chim. Acta*, 24:203.

Zalipsky, S. (1993) "Synthesis of an end group functionalized polyethylene glycol–lipid conjugate for preparation of polymer grafted liposomes," *Bioconjugate Chem.*, 4:296–299.

Leserman, L.D., et al. (1980) "Targeting to cells of fluorescent liposomes covalently coupled with monoclonal antibody or protein A," *Nature*, 288:602–604.

Loughrey, H., et al. (1987) "A non–covalent method of attaching antibodies to liposomes," *Biochimica et Biophysica Acta*, 901:157–160.

Heath, T.D., et al. (1983) "Antibody targeted liposomes: Increase in specific toxicity of methotrexate–γ–aspartate," *Proceedings of the National Academy of Sciences, USA*, 80:1377–1381.

Wolff, B., et al. (1984) "The use of monoclonal anti–THy$^1$IgG$_1$ for the targeting of liposomes to AKR–A cells in vitro and in vivo," *Biochimica et Biophysica Acta*, 802:259–273.

Martin, F.J., et al. (1982) "Irreversible coupling of immunoglobulin fragments to preformed vesicles. An improved method for liposome targeting," *Journal of Biological Chemistry*, 257(1):286–288.

Kondejewski, L.H., et al. (1994) "Synthesis and characterization of carbohydrate–linked murine monoclonal antibody K20—human serum albumin conjugates," *Bioconjugate Chemistry* 5:602–611.

GLYCOSYLATED PROTEIN-LIPOSOME CONJUGATES AND METHODS FOR THEIR PREPARATION

This application is a continuation-in-part of U.S. Ser. No. 08/418,696, filed Apr. 7, 1995, now abandoned, which is a continuation-in-part of U.S. Ser. No. 08/316,394, filed Sep. 30, 1994, now abandoned.

BACKGROUND OF THE INVENTION

Liposomes are vesicles produced from bilayer forming lipids and are currently of interest as drug delivery vehicles. Liposomal formulations are capable of altering the biodistribution of drugs which, in certain cases, results in reduced toxicity and/or an improvement in the therapeutic index of the drug. The biodistribution of liposomes may be altered by changing the size or lipid composition. An alternative procedure of current interest for altering biodistribution involves the conjugation of targeting vectors to the liposomal surface (see, Heath, et al., Chem. Phys. Lipids 40:347 (1986)). Such vectors should allow tissue specific accumulation of the drug. The targeting vectors usually used are antibodies specific for an antigen expressed mostly by the targeted tissue.

A number of different protocols for the conjugation of antibodies to the surface of liposomes have been developed. In one type of protocol, antibodies have been bound to liposomes which have protein A or protein G conjugated to their surfaces. See, Leserman, et al., Nature 288:602–604 (1980). Protein A and protein G bind to the Fc portion of antibodies, allowing, in principle, both antigen binding sites to be available. A disadvantage of the procedure is the difficulty in selectively derivatizing the protein A or G so that it is correctly orientated and capable of binding the antibody. Additionally, the conjugated protein A or G may, in some cases, induce an immunogenic response. Moreover, the protocols used to conjugate the protein A or G may also cause formation of ternary liposome-protein-liposome complexes.

A similar type of protocol uses avidin or streptavidin conjugated to liposomes to bind biotinylated antibodies. See, Loughrey, et al., Biochimn. Biophys. Acta 901:157–160 (1987). However, it is difficult to control aggregation with these systems since crosslinking can occur during the avidin conjugation step or on exposure to the biotinylated antibody.

A third type of protocol involves direct coupling of the antibody to the liposomal surface. Usually this is achieved by modification of the antibody's amino functions with a crosslinking agent such as N-succinimidyl-3-(2-pyridyldithio)propionate (SPDP). See, Heath, et al., Proc. Natl. Acad. Sci. USA 80:1377–1381 (1983). However, such modifications are not selective and (i) may damage the antigen binding site (ii) may not orientate the antibody in such a manner that the antigen binding sites are available for binding. In addition, such liposomes may aggregate during derivitization and be rapidly cleared in vivo due to Fc receptor mediated recognition by the immune system.

Alteratively, antibodies may be coupled to the liposomal surface after mild oxidation of the carbohydrate functions located in the $C_H{}^2$ domain of the Fc fragment. These procedures allow selective modification of the antibody such that (i) the antigen binding sites are not damaged (ii) the antigen binding sites are always directed outward from the liposome surface (see, Domen, et al., J. Chromatography 510:293 (1990)). The most common procedure of this sort involves coupling the oxidized antibody to a liposome surface containing amino functions by reductive amination using sodium cyanoborohydride. Aggregation may result from such systems due to reductive amination occurring with the amino functions of a second antibody. A potentially more useful procedure involves conjugation of the oxidized antibody directly to hydrazide functions on the liposome surface (see, Chua, et al., Biochim. Biophys. Acta 800:291 (1984)). The disadvantage of the latter systems lies with the poor anchoring ability of short single acyl chains. In addition, the hydrazide-aldehyde reaction proceeds at a lower rate than the more commonly used thiol-maleimide reaction. Consequently, long reaction times may be required to effect adequate conjugation between the protein and liposome surfaces. Related compounds reported by Zalipsky, Bioconjugate Chem. 4:296–299 (1993), the disclosure of which are incorporated herein by reference, could potentially be used in a similar manner.

What is needed in the art is a new procedure for linking glycosylated proteins to liposomes which avoids the above problems and provides compositions capable of delivering therapeutic agents to their sites of action. Surprisingly, the present invention provides such compositions and methods.

SUMMARY OF THE INVENTION

The present invention provides glycosylated protein-liposome compositions which are useful for the targeted delivery of a therapeutic agent. The compositions comprise an oxidized glycosylated protein, typically an antibody, which is covalently attached to a lipid by means of a crosslinking agent having an acid hydrazide functionality on one terminus and a sulfhydryl functionality on the other terminus. The lipid is present in a liposome formulation. Methods for preparing the compositions are also provided. In the methods, a glycosylated protein is first oxidized then reacted with a linking group (present in excess) having an acid hydrazide on one end and a sulfhydryl or protected sulfhydryl group on the other end. The resultant modified protein is then reacted with a liposome formulation of a lipid having a sulfhydryl reactive functional group to covalently attach the protein to the liposome.

The compositions and methods of the present invention provide a number of advantages over existing compositions and methods, namely (i) liposomal systems utilizing thiol reactive groups are well known and characterized, (ii) the conjugate may be stably anchored, (iii) the antigen binding sites of the antibody are not damaged, and (iv) the antigen binding sites are directed away from the liposome surface.

DETAILED DESCRIPTION OF THE INVENTION

Abbreviations and Definitions

Figure 1:
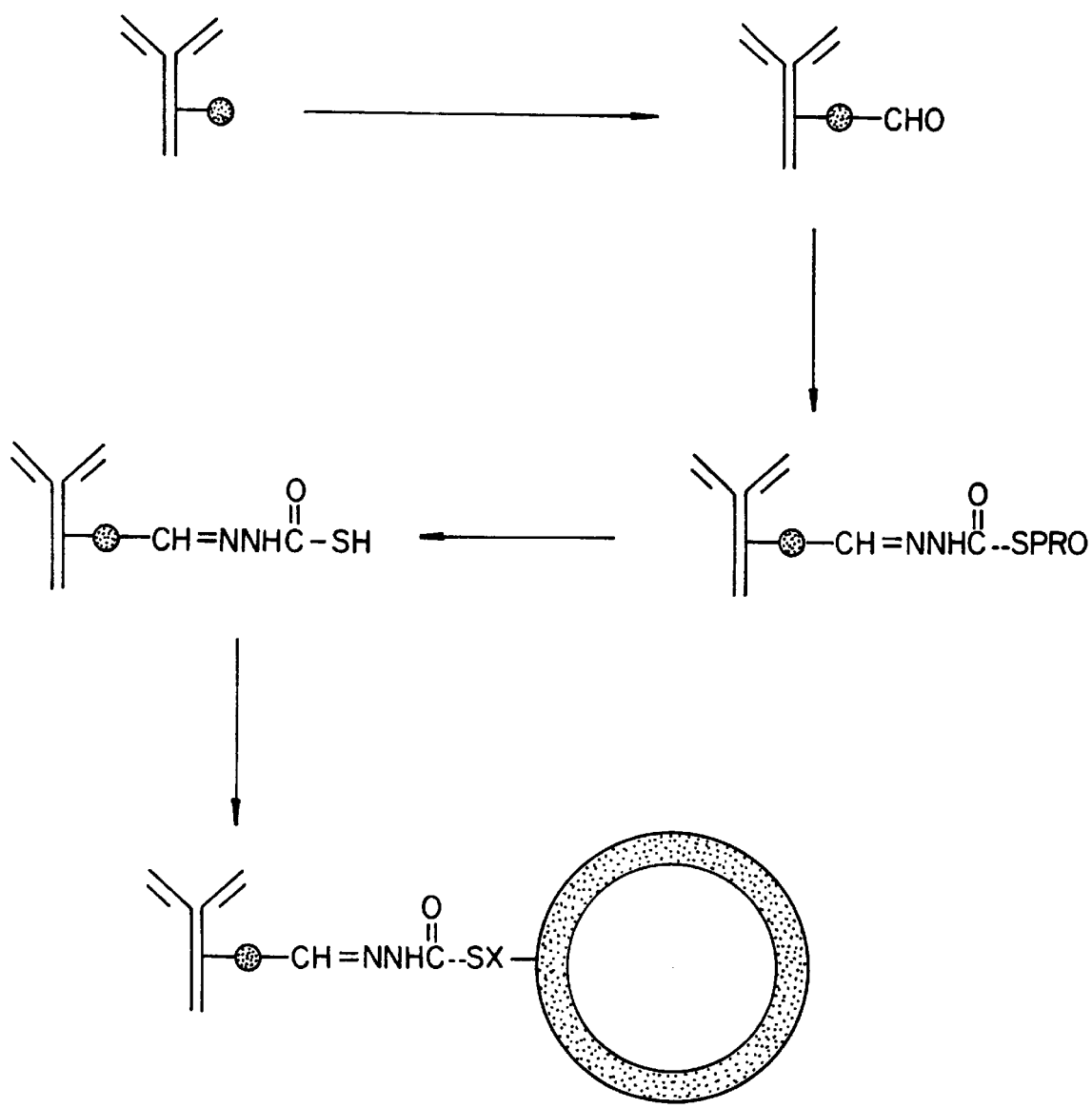
FIG. 1 is a scheme illustrating one method of preparing the IgG-conjugates of the present invention.

Abbreviations used herein have the following meanings: DTT, dithiothreitol; MPB-DPPE, N-(4-(p-maleidophenyl) butyryl)-1,2-sn-dipalmitoylphosphatidylethanolamine; IAX-DPPE, N-((6-(iodoacetyl)amino)hexanoyl)-1,2-sn-dipalmitoylphosphatidylethanolamine; MPB-DSPE, N-(4-(p-maleidophenyl)butyryl)-1,2-sn-distearoylphosphatidylethanolamine; IAX-DSPE, N-((6-(iodoacetyl)amino)hexanoyl)-1,2-sn-distearoylphosphatidylethanoiarine; PDPH, 3-(2-pyridyldithio)propionic acid hydrazide hydrochloride; PBS, phosphate buffered saline; SPDP, N-succinimidyl 3-(2-pyridyldithio)propionate; SAS, sodium acetate saline; DSPC, 1,2-sn-distearoylphosphatidylcholine; HEPES, N-(2-hydroxyethyl)piperidine-N-2-ethanesulphonic acid; HBS, HEPES buffered saline; MLV, multilammelar vesicles.

As used herein, the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "alkoxy" and similar terms. Preferred alkyl groups are those containing 1 to 10 carbon atoms, while those containing 1 to 5 carbon atoms are particularly preferred. All numerical ranges in this specification and claims are intended to be inclusive of their upper and lower limits. When alkyl is used to refer to a linking group, it is taken to be a group having two available valences for covalent attachment, for example, —CH$_2$CH$_2$—, —CH$_2$CH$_2$CH$_2$—, —CH$_2$CH$_2$CH(CH$_3$)CH$_2$— and —CH$_2$(CH$_2$CH$_2$)$_2$CH$_2$—. Preferred alkyl groups as linking groups are those containing 1 to 11 carbon atoms, with those containing 2 to 6 carbon atoms being particularly preferred. The term "alkenyl" refers to alkyl groups having one or more double bonds. When "alkenyl" is used to refer to a linking group, it is taken to be a group having two available valences for covalent attachment, for example, —CH=CHCH$_2$—, —CH$_2$CH=C (CH$_3$)CH$_2$— and —CH=CH—CH=CH—(CH$_2$CH2)$_2$CH$_2$—.

The term "alkoxy" refers to an alkyl radical as described above which also bears an oxygen substituent which is capable of covalent attachment to another hydrocarbon radical (such as, for example, methoxy, ethoxy and t-butoxy).

As used herein, the term "protecting group" refers to any group which temporarily blocks one reactive site in a multifunctional compound while a chemical reaction is carried out selectively at another reactive site.

As used herein, the term "sulfhydryl-reactive functionality" refers to any reactive groups which are capable of interacting with a sulfhydryl group to form a new covalent bond. Examples of sulfhydryl-reactive functionalities include haloacetyl groups (which upon reaction with a sulfhydryl group, form a thioether), disulfides (which form new disulfides), sulfhydryl groups (which form disulfides) and maleimides (which form thioethers).

The term "protein" refers to a polypeptide or polyaminoacid which can be either naturally occurring or synthetic. The term "glycosylated protein" refers to proteins having attached carbohydrate residues.

As used herein, the term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgO, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

As used herein the term "antibody" includes the various forms above, as well as single chain forms, which have present a carbohydrate group which can be oxidized for use in the present invention and which when oxidized will not interfere with antigenic recognition. Methods of producing antibodies suitable for use in the present invention are well known to those skilled in the art and can be found described in such publications as Harlow & Lane, *Antibodies: A Laboratory Manual,* Cold Spring Harbor Laboratory, (1988). "Monoclonal antibodies" may be obtained by various techniques familiar to those skilled in the art. Briefly, spleen cells from an animal immunized with a desired antigen are immortalized, commonly by fusion with a myeloma cell (see, Kohler and Milstein, Eur. *J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

As used herein, the term "tissue" refers to any pathological cell or group of cells that exhibit a similar pathological trait. For example, the trait may be malignant transformation. Alternatively, the trait may be intracellular infection. Generally, the tissue will include cells that originate from the same cell type.

DESCRIPTION OF THE EMBODIMENTS

The present invention provides novel glycosylated protein-liposome compositions and methods for their preparation. The compositions are prepared by a novel procedure in which a glycosylated protein is oxidized and conjugated to a crosslinking agent having both a hydrazide function and a free or protected thiol function. This results in the introduction of a tethered thiol function which can then be conjugated to a thiol reactive function on a liposome surface to provide the glycosylated protein-liposome compositions.

Thus in one aspect, the present invention provides glycosylated protein-liposome compositions of formula I:

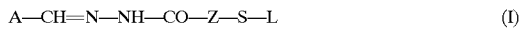

A—CH=N—NH—CO—Z—S—L (I)

In this formula, the letter A represents an oxidized glycosylated protein, the letter L represents a liposome, and the letter Z represents the hydrocarbon backbone of a crosslinking group. The hydrocarbon backbone is a $C_1$–$C_{11}$ alkyl linking group or a $C_1$–$C_{11}$ alkenyl linking group, either of which is optionally substituted by one or more hydroxy (—OH), amino (—NH$_2$), alkoxy (—OR), alkylamino (—NHR), dialkylamino (—NRR'), acyloxy (—OCOR) or carbamoyl (—NHCOR) groups.

The proteins, A, used in constructing the compositions of the present invention can be any glycosylated protein. Preferred proteins are those which can be covalently attached to a liposome by means of a crosslinking group and which maintain their ability to bind to their natural target (i.e., a receptor site, an antigen, or other binding site). Glycosylated proteins which are useful in the present compositions include antibodies (i.e., immunoglobulins such as IgG, IgM and IgE), monoclonal antibodies, immunomodulators (i.e., IL-1 and IL-2), avidin and tumor necrosis factor (TNF). The protein, after oxidation, is covalently attached to a crosslinking group by means of a hydrazone.

The crosslinking group is a linking group which, prior to attachment to the protein and liposome, has two reactive functionalities which can be reacted independently. The backbone of the crosslinking group is a hydrocarbon chain, Z, having from 1 to 11 carbon atoms, preferably from 1 to 5 carbon atoms, and more preferably 2 carbon atoms. The hydrocarbon chain can be either saturated or unsaturated and is optionally substituted with one or more hydroxy (—OH), amino (—NH$_2$), alkoxy (—OR), alkylamino (—NHR), dialkylamino (—NRR'), acyloxy (—OCOR) or carbamoyl (—NHCOR) groups, wherein R and R' each represent a $C_1$–$C_5$ alkyl group. The reactive functionalities are attached at each terminus of the hydrocarbon chain. Thus, at one terminus is an acid hydrazide group which, when reacted with an oxidized glycosylated protein, forms a covalent hydrazone linkage. At the other terminus of the hydrocarbon chain is a sulfhydryl group, optionally in a protected form, which is reacted with a reactive liposome having at least one sulfhydryl-reactive functionality to form a covalent linkage and provide a glycosylated protein-liposome complex.

The reactive liposomes which are used in formation of the compositions of the present invention will be composed of at least one lipid having a sulfhydryl reactive functional group. The sulfhydryl reactive functional group can be any of a variety of groups capable of forming covalent linkages upon contact with a free sulfhydryl moiety. Examples of sulfhydryl reactive groups include haloacetyl, disulfide, maleimido and sulfhydryl. Preferred lipids having sulfhydryl-reactive functional groups are N-(4-(p-maleidophenyl)butyryl)-1,2-sn-dipalmitoylphosphatidylethanolamine and N-((6-(iodoacetyl)amino)hexanoyl)-1,2-sn-dipalmitoylphosphatidylethanolamine which are available from commercial sources. Alternatively, such modified lipids can be prepared by methods known to those of skill in the art, and described in, for example, Wolff, et al., *Biochim. Biophys. Acta* 802:259–273 (1984) and Martin, et al., *J. Biol. Chem.* 257:286–288 (1982), the disclosures of which are incorporated herein by reference. In addition to the lipids having a sulfhydryl reactive functional group, the reactive liposomes in the present invention will include other traditional liposome producing lipids. The traditional liposome producing lipids can be natural or synthetic lipids.

Typically, the major lipid component in the reactive liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Phosphatidylcholines (e.g., egg phosphatidylcholine) containing saturated fatty acids with carbon chain lengths in the range of $C_{14}$ to $C_{22}$ are preferred. Phosphatidylcholines with mono or diunsaturated fatty acids and mixtures of saturated and unsaturated fatty acids may also be used. Liposomes useful in the present invention may also be composed of sphingomyelin or phospholipids with head groups other than choline, such as ethanolamine, serine, glycerol and inositol. In particular, phospholipids suitable for formation of liposomes useful in the methods and compositions of the present invention include, e.g., phosphatidylcholine, phosphatidylglycerol, lecithin, β, γ-dipalmitoyl-α-lecithin, sphingomyelin, phosphatidylserine, phosphatidic acid, phosphatidylethanolamine, lysolecithin, lyso-phosphatidylethanolamine, phosphatidylinositol, cephalin, cardiolipin, dicetylphosphate, dioleoylphosphatidylcholine, dipalmitoylphosphatidylcholine, dipalmitoylphosphatidylglyceryl, dioleoylphosphatidylglycerol, palmitoyl-oleoylphosphatidylcholine, di-stearoyl-phosphatidylcholine, stearoyl-palmitoylphosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposomes of the compositions of the present invention. These include, e.g., diacylglycerols, cerebrosides, N-(2,3-di(9-(Z)-octadecenyloxy))-prop-1-yl-N,N,N-trimethylammonium chloride, stearylamine, dodecylamine, acetyl palmitate, fatty acid amides, and the like. Additional lipids suitable for use in the liposomes of the present invention are well known to persons of skill in the art and are cited in a variety of well known sources, e.g., *McCutcheon's Detergents and Emulsifiers* and *McCutcheon's Functional Materials*, Allured Publishing Co., Ridgewood, N.J., both of which are incorporated herein by reference. Preferred liposomes will include a sterol, preferably cholesterol, at molar ratios of from 0.1 to 1.0 (cholesterol:phospholipid).

In one group of embodiments, the liposomes used in the present compositions further comprise a steric barrier component. These components are known to inhibit liposome-liposome interactions and thereby reduce aggregation of the liposome systems formed. Suitable steric barrier components are modified derivatives of lipids and cholesterol, such as polyethylene glycol derivatives of cholesterol (PEG-cholesterols) and PEG-lipids (e.g., phosphatidyl-ethanolamine-polyoxyethylene conjugates and phosphatidic acid-polyoxyethylene conjugates). The polyoxyethylene conjugates which are used in the compositions of the present invention can be prepared by combining the conjugating group (i.e. phosphatidic acid or phosphatidylethanolamine) with an appropriately functionalized polyoxyethylene derivative. For example, phosphatidylethanolamine can be combined with ω-methoxypolyethyleneglycol succinate to provide a phosphatidylethanolamine-polyoxyethylene conjugate. See, Parr, et al., *Biochim. Biophys. Acta* 1195:21–30

(1994), incorporated herein by reference. Where present, the PEG-cholesterol or PEG-lipids will comprise from 0.5 to about 5.0 mole % of the total lipid composition. Other PEG-modified lipids are described in co-pending application Ser. No. 08/486,214 now U.S. Pat. No. 5,820,873, (e.g. MePEGS-2000-Cer).

A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta,* 443:629–634 (1976); Fraley, et al., *Proc. Natl. Acad. Sci. USA,* 76:3348–3352 (1979); Hope, et al., *Biochim. Biophys. Acta,* 812:55–65 (1985); Mayer, et al., *Biochim. Biophys. Acta,* 858:161–168 (1986); Williams, et al., *Proc. Natl. Acad. Sci.,* 85:242–246 (1988), the text *Liposomes,* Marc J. Ostro, ed., Marcel Dekker, Inc., New York, 1983, Chapter 1, and Hope, et al., *Chem. Phys. Lip.* 40:89 (1986), all of which are incorporated herein by reference. Suitable methods include, e.g., sonication, extrusion, high pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Unilamellar vesicles are generally prepared by sonication or extrusion. Sonication is generally performed with a tip sonifier, such as a Branson tip sonifier, in an ice bath. Typically, the suspension is subjected to several sonication cycles. Extrusion may be carried out by biomembrane extruders, such as the LIPEX BIOMEMBRANE EXTRUDER®. Defined pore size in the extrusion filters may generate unilamellar liposomal vesicles of specific sizes. The liposomes may also be formed by extrusion through an asymmetric ceramic filter, such as a CERA-FLOW MICROFILTER®, commercially available from the Norton Company, Worcester Mass.

Following liposome preparation, the liposomes which have not been sized during formation may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high throughput basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.,* 10:421–450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of from about 0.05 microns to about 0.20 microns are preferred.

The protein-liposome complexes of the present invention are useful for the targeted delivery of therapeutic agents and are also useful in diagnostic assays.

For the delivery of therapeutic agents, the compositions can be loaded with a therapeutic agent and administered to the subject requiring treatment. The therapeutic agents which are administered using the present invention can be any of a variety of drugs which are selected to be an appropriate treatment for the disease to be treated in the tissue. Often the drug will be an antineoplastic agent, such as vincristine, doxorubicin, mitoxantrone, camptothecin, cisplatin, bleomycin, cyclophosphamide, methotrexate, streptozotocin, and the like. It may also be desirable to deliver antiinfective agents to specific tissues by the present methods. The compositions of the present invention can also be used for the selective delivery of other drugs including, but not limited to local anesthetics, e.g., dibucaine and chlorpronazine; beta-adrenergic blockers, e.g., propranolol, timolol and labetolol; antihypertensive agents, e.g., clonidine and hydralazine; anti-depressants, e.g., imipramine, amitriptyline and doxepim; anti-convulsants, e.g., phenytoin; antihistamnines, e.g., diphenhydranine, chlorphenimine and promethazine; antibiotic/antibacterial agents, e.g., gentamicin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents. Other particular drugs which can be selectively administered by the compositions of the present invention will be well known to those of skill in the art. Additionally, two or more therapeutic agents may be administered simultaneously if desired, where such agents produce complementary or synergistic effects. Methods of loading conventional drugs into liposomes include an encapsulation technique and the transmembrane potental loading method.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. No. 4,885,172, U.S. Pat. No. 5,059,421, and U.S. Pat. No. 5,171,578, the contents of which are incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., $Na^+$, $K^+$ and/or $H^+$) across the membranes. This concentration gradient is generated by producing liposomes having different internal and external media. Thus, for a drug which is negatively charged when ionized, a transmembrane potential is created across the membranes which has an inside potential which is positive relative to the outside potential. For a drug which is positively charged, the opposite transmembrane potential would be used.

The protein-liposome complexes of the present invention can be administered to a subject according to standard techniques. Preferably, pharmaceutical compositions of the protein-liposome complexes are administered parenterally, i.e., intraarticularly, intravenously, subcutaneously, or intramuscularly. More preferably, the pharmaceutical compositions are administered intravenously by a bolus injection. Suitable formulations for use in the present invention are found in *Remington's Pharmaceutical Sciences,* Mack Publishing Company, Philadelphia, Pa., 17th ed. (1985). The pharmaceutical compositions can be used to diagnose a variety of conditions, for instance inflammation associated with rheumatoid arthritis, post-ischemic leukocyte-mediated tissue damage (reperfusion injury), acute leukocyte-mediated lung injury (e.g., adult respiratory distress syndrome), septic shock, and acute and chronic inflammation, including atopic dermatitis and psoriasis. In addition, various neoplasms and tumor metastases can be detected.

Preferably, the pharmaceutical compositions are administered intravenously Thus, this invention provides compositions for intravenous administration which comprise a solution of the liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of protein-liposome complexes, in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For diagnosis, the amount of composition administered will depend upon the particular label used (i.e., radiolabel, fluorescence label, and the like), the disease state being diagnosed and the judgement of the clinician, but will generally be between about 1 and about 5 mg per kilogram of body weight.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and thus having shorter half-lives in the bloodstream. Liposomes with prolonged circulation half-lives are typically desirable for therapeutic and diagnostic uses. One means of increasing circulation half-life is the incorporation of $GM_1$ or phospholipid-polyoxyethylene conjugates in the liposome formulation. For instance, liposomes which can be maintained from 8, 12, or up to 24 hours in the bloodstream are particularly preferred.

Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

In addition to therapeutic treatments, the protein-liposome compositions of the present invention are useful in diagnostic assays. The amount of the protein-liposome complex used will depend on the sensitivity of the liposome-coupled antibody to the target antigen, as well as the particular label and detection methods which are used.

In another aspect, the present invention provides methods for the preparation of the compositions of formula I. In broad terms, the method involves (a) oxidizing a glycosylated protein to form a protein having at least one reactive aldehyde functionality; (b) reacting the oxidized protein with a crosslinking group having both a hydrazide functionality and a sulfhydryl or protected sulfhydryl functionality to form a covalent hydrazone linkage and provide a modified protein having a tethered sulfhydryl derivative; and (c) contacting a reactive liposome having a sulfhydryl-reactive functionality with the modified protein under conditions sufficient to covalently attach the liposome to the modified protein and thereby form the protein-liposome complex. This process is presented schematically in FIG. 1.

As with the compositions above, the glycosylated protein used in the method of the present invention can be any of a variety of glycosylated proteins. Glycosylated proteins which are useful in the present compositions include antibodies (i.e., immunoglobulins such as IgG, IgM and IgE), monoclonal antibodies, immunomodulators (i.e., IL-1 and IL-2), avidin and tumor necrosis factor ( Preferably, the protein will be an antibody which is generated either to an antigen present in a diseased or compromised tissue or to an antigen present on a cell surface such as a cancer cell. The proteins used in the present invention can be obtained from commercial sources, isolated from natural products, or prepared according to protocols known to those of skill in the art. In preferred embodiments the glycosylated proteins include IgG, anti-CD4 (available from CedarLane Laboratories, Hornby, Ontario, Canada), anti-CD8 (from CedarLane Laboratories), anti-ICAM-1 (available from R & D Systems, Inc., Minneapolis, Minn., USA), anti-ICAM-2, CC49, α-Erb-B2, α-CEA, and pancarcinoma antibodies, as well as proteins such as avidin.

The reagents and conditions used for oxidizing the glycosylated protein are not critical but should be sufficiently mild so that the protein retains a substantial portion of its binding affinity for the target. More particularly, the oxidation methods would include those methods which oxidize a primary alcohol to an aldehyde. These methods are known to one of skill in the art and can be found in, for example, March, *Advanced Organic Chemistry, 4th Ed.* Wiley-Interscience, New York, N.Y., p. 1167–1171 (1992), incorporated herein by reference. In preferred embodiments, the oxidizing agent used is sodium metaperiodate. In another group of embodiments, the oxidized protein is separated from any excess oxidizing agent or side products by gel filtration on, for example, a SEPHADEX® column.

Following oxidation, the protein is covalently attached to a crosslinking agent of formula (II)

$$H_2N-NH-CO-Z-S-Q \quad (II)$$

In formula II, the letter Z represents either a $C_1$–$C_{11}$ alkyl linking group or a $C_1$–$C_{11}$ alkenyl linking group. Each of these groups is optionally substituted by one or more of the following: —OH, —OR, —$NH_2$, —NHR, —NRR', —NHCOR and —OCOR, wherein R and R' each represent $C_1$–$C_5$ alkyl. The letter Q represents either a sulfhydryl protecting group or a hydrogen. A number of sulfhydryl protecting groups are known to those of skill in the art and can be found, with references for their preparation and removal, in Greene, et al., *Protective Groups In Organic Chemistry, Second Ed,* Wiley-Interscience, New York, N.Y., Chapter 6, pages 277–308 (1991), incorporated herein by reference. Preferred sulfhydryl protecting groups are those which can be removed under conditions which will not affect the attached protein. Examples of suitable sulfhydryl protecting groups are 2-pyridylthio and S-acetyl. Covalent attachment of the oxidized protein to the crosslinking agent occurs via formation of a hydrazone (from the newly formed aldehyde in the oxidized protein and the acid hydrazide in the crosslinking agent). In preferred embodiments, the letter Z in formula II represents a $C_1$–$C_5$ alkyl linking group, more preferably a —$(CH_2)_2$— group.

The modified protein formed by the attachment of the oxidized protein to the crosslinking agent has a tethered sulfhydryl derivative. The sulfhydryl derivative is either a sulfhydryl radical (—SH) or a protected sulfhydryl group (—SQ). In one group of embodiments, the protecting group is removed prior to reacting the modified protein with a reactive liposome. In another group of embodiments, a disulfide protecting group can remain attached while reacting the modified protein with a liposome having, for example, a reactive sulfhydryl group. In this manner, the sulfhydryl group which is part of the liposome can participate in disulfide exchange to provide the compositions of the present invention while at the same time, removing the sulfhydryl protecting group.

The reactive liposomes used in the methods of the present invention are the same as those discussed above with regard to the compositions and will include at least one lipid having a sulfhydryl reactive functional group. The sulfhydryl reactive functional group can be any of a variety of groups capable of forming covalent linkages upon contact with a free sulfhydryl moiety. Examples of sulfhydryl reactive groups include haloacetyl, disulfide, maleimido and sulfhydryl. Preferred sulfhydryl reactive functional groups are iodoacetyl and maleido groups. Preferred lipids having sulfhydryl-reactive functional groups are N-(4-(p-maleidophenyl)butyryl)-1,2-sn-dipalmitoylphosphatidylethanolamine, N-(4-(p-maleidophenyl)butyryl)-1,2-sn-distearoylphosphatidylethanolamine, N-((6-(iodoacetyl)amino)hexanoyl)-1,2-sn-distearoylphosphatidylethanolamine and N-((6-(iodoacetyl)amino)hexanoyl)-1,2-sn-dipalmitoylphosphatidylethanolamine which are available from commercial sources. Alternatively, such modified lipids can be prepared by methods known to those of skill in the art. In a particularly preferred embodiment, the reactive liposome used in the present invention comprises MPB-DPPE, DSPC and cholesterol. The conditions used for covalent attachment of the modified protein to the reactive liposome will depend on the nature of the linkage being formed and can be determined by one skilled in the art. Typically, the conditions will involve reacting the modified protein with the reactive liposome in an aqueous buffer system at room temperature. Elevated temperatures can be used provided that denaturation of the protein does not occur. Progress of complex formation can be monitored by assaying aliquots which have been chromatographed using both a phosphate assay for lipid content and a BCA assay for protein content. The phosphate assay has been described (see, Bottscher, et al., *Anal. Chim. Acta,* 24:203 (1961)). The BCA assay is available from Pierce Chemical Co.

The following examples are offered solely for the purposes of illustration, and are intended neither to limit nor to define the invention.

EXAMPLES

Materials 3-(2-pyridyldithio)propionic acid hydrazide hydrochloride (PDPH) was obtained from BioAffinity Systems, Inc., Roscoe, Ill., USA. 1,2-distearoyl-sn-glycero-3-phosphocholine (DSPC) was purchased from Avanti Polar Lipids Birmingham, Ala., USA. N-(4-(p-maleimidophenyl)butyryl)-dipalmitoylphosphatidylethanolamie (MPB-DPPE) and MePEG$_{2000}$-S-DSPE (PEG-DSPE) were obtained from Northern Lipids Inc., Vancouver, Canada. MePEGS-2000-Cer (1-O-(2'-(ω-methoxypolyethyleneglycol)succinoyl)-2-N-arachidoylsphingosine) was prepared by methods described in co-pending application U.S. Ser. No. 08/486,214, filed Jun. 7, 1995; N-succinimidyl 3-(2-pyridyldithio)propionate (SPDP) and the micro BSA protein assay kit were obtained from Pierce (Rockford, Ill., USA). Cholesterol, N-(2-hydroxyethyl) piperazine-N'-(2-ethanesulphonic acid) (HEPFS), SEPHAROSE® CL-4B, SEPHAROSE CL-6B, SEPHADEX® G-25, SEPHADEX® G-50, SEPHADEX® G-50-80, dithiothreitol (DTT), 5,5'-dithiobis(2-nitrobenzoic acid) [Ellmans reagent], 1-amino-2-naphthol-4-sulfonic acid, human IgG and sodium periodate were obtained from Sigma Chemical Company, St. Louis, Mo., USA. Cholesteryl [$^3$H] hexadecyl ether ([$^3$H]-CHE) was obtained from Amersham (Oakeville, Ontario, Canada). Doxorubicin was obtained from Pharmacia, Inc., Mississauga, Ontario, Canada; anti-human IgG was obtained from Jackson Laboratories, Bar Harbor, Me., USA; ammonium molybdate, sodium chloride, NaHSO$_3$, Na$_2$SO$_3$, anhydrous sodium acetate were obtained from BDH (via VWR Scientific, Edmonton, Alberta, Canada). The tumor cell line LS180 was obtained from the ATCC. The NRLU-10 murine monoclonal antibody was a gift from NeoRx. Female CD1 mice were obtained from Charles River.

HEPES buffered Saline (HBS) was prepared as follows: A solution of HEPES (4.77 g) and sodium chloride (8.77 g) in distilled water (1 L) was adjusted to pH 7.4 with 5M sodium hydroxide solution. SAS was prepared as a 100 mM sodium acetate and 50 mM sodium chloride solution at pH 4.4. Fisck reagent was prepared by dissolving 150 g of NaHSO$_3$, 5 g of Na$_2$SO$_3$ and 2.5 g of 1-amino-2-naphthol-4-sulfonic acid in 1 L of water.

The Lipex extruder was obtained from Lipex Biomembranes, Vancouver, Canada.

EXAMPLE 1

This example illustrates a comparison of SPDP and PDPH as crosslinking groups for human IgG-liposome conjugates.

Preparation of liposomes. Liposomes were prepared by an extrusion procedure described in Hope, et al., *Biochim. Biophys. Acta* 812:55–65 (1985). Briefly, lipid mixtures of the appropriate composition were dissolved in chloroform and concentrated to a homogeneous film under a nitrogen stream in a warm water bath. The film was then dried overnight in a lyophilizer. The dried lipid was hydrated in HBS at 67° C. and the resultant multilammelar vesicles frozen in liquid nitrogen and thawed at 67° C. five times before being extruded through stacked polycarbonate 100 nm filters (Nucleopore) using an extrusion press device (Lipex Biomembranes, Inc., Vancouver, Canada) at 65° C.

Thiolation of IgG using SPDP. An IgG solution in PBS was treated with 5 mol equivalents of SPDP in ethanol, such that the final ethanol content was less than 4%, for thirty minutes. The reaction mixture was passed down a SEPHADEX® G-50 column equilibrated in SAS to isolate the derivatized antibody and replace the buffer. Fractions with an absorbance at 280 nm greater than 1.0 were combined and DTT was added by weight (3.8 mg/mL). The solution was stirred at room temperature for twenty minutes and then passed down a SEPHADEX® G-50 column equilibrated in HBS to isolate the thiolated antibody and replace the buffer. The protein concentration was determined from the absorbance at 280 nm (mg/mL=A$_{280}$/1.35).

Thiolation of IgG using PDPH. An IgG solution in PBS was oxidized with sodium periodate (1 mg per mL of final solution, dissolved in 0.2 mL of distilled water) at room temperature for one hour. The antibody was isolated and the buffer was exchanged by gel filtration (SEPHADEX® G-50 equilibrated in SAS). Fractions with an absorbance at 280 nm greater than 1.0 were combined and treated with 0.1M PDPH in ethanol (40 μL per mL of IgG solution) at room temperature with stirring for five hours. The antibody was isolated by gel filtration (SEPHADEX® G-50 equilibrated in SAS) and treated with DTT (3.86 mg/mL of IgG solution) for twenty minutes. The reaction mixture was centrifuged for the final five minutes to pellet out any precipitated material. The thiolated antibody was isolated and the buffer was exchanged by gel filtration (SEPHADEX® G-50 equilibrated in HBS). The protein concentration was determined from the absorbance at 280 nm (mg/mL=A$_{280}$/1.35).

Conjugation of thiolated IgG to liposomes. A solution of thiolated antibody was treated with liposomes at ratio of 75–150 μg protein per μmol lipid with stirring for an appropriate time, usually 16 hours. The reaction was stopped by passing the mixture down a SEPHAROSE® CL-4B column equilibrated with HBS. The protein and lipid concentrations were assayed to determine the degree of conjugation. The size of the conjugates were determined by a Nicomp particle sizer.

Lipid assays. The lipid assay is based on phosphate content. Briefly, samples with an estimated phosphate content in the range 50–150 nmol were digested in perchloric acid (0.7 mL) at 180° C. for one hour. The samples were allowed to cool. Ammonium molybdate solution (7 mL, prepared by dissolving 4.4 g of ammonium molybdate in 2 L of distilled water and 40 mL of sulfuric acid) and Fiske reagent (0.7 mL) were added and the solutions were vortexed. The solutions were heated in a boiling water bath for thirty minutes, allowed to cool and assayed relative to a standard curve (0, 50, 100, 200 nmol phosphate) at 512 nm.

Protein assays. Protein was assayed using a modification of the protocol for the micro BCA protein assay kit from Pierce. A set of bovine serum albumin standards containing 2.5–20 μg of protein and samples containing 0.333 μmol of lipid were diluted with 5% TRITON X-100 (100 μL) and sufficient distilled water to produce a total volume of 1.0 mL. The working reagent (1.0 mL) was then added and the solution was vortexed to ensure mixing. The solutions were incubated at 60° C. for one hour, allowed to cool and the protein concentrations of the samples were determined relative to the standards from the absorbance at 562 nm. Control liposomes (without protein conjugated on the surface) consistently assay at less than 1 μg protein/μmol lipid.

Sulfhydryl assays. The protein concentration of the IgG solution to be assayed was determined from the absorbance at 280 nm. Ellman's reagent (60 μL of a 4 mg/mL solution in HBS) was added to 0.600 mL aliquots of a control and the samples in HBS, and allowed to incubate at room temperature for twenty minutes. Sulfhydryl levels were determined from the absorbance at 412 nm (ε=13600), relative to the control.

Figure 2:
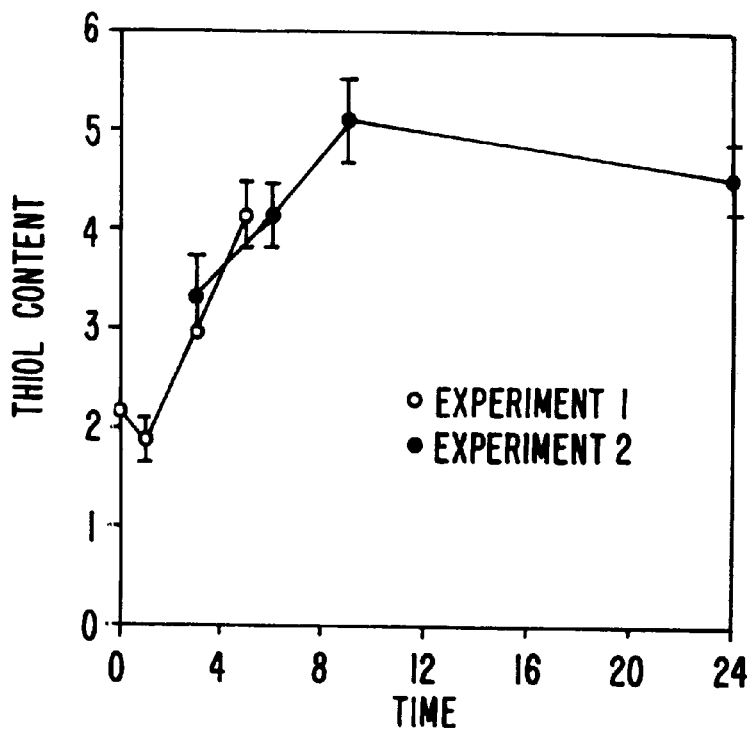
FIG. 2 is a graph showing the thiol content of the conjugate initially formed from oxidized human IgG and PDPH with respect to DTT incubation time.

Optimization of PDPH incubation time. Oxidized human IgG was produced and treated with PDPH as described above. Aliquots were removed after 0, 1, 3 and 5 hours and passed down a SEPHADEX® G-50 column in SAS to stop the reaction. Fractions with an absorbance at 280 nm of greater than 1.0 were pooled and treated with DTT (3.86 mg/mL of IgG solution) for 20 min. The solution was centrifuged at 2000 rpm for the final five minutes and the supernatant was passed down a SEPHADEX® G-50 column in HBS. Fractions with an absorbance of greater than 0.5 were analyzed for sulfhydryl content as described above. The mean value was used for the data point The experiment was repeated using aliquots taken after 3, 6, 9 and 24 hours, and the combined data is plotted in FIG. 2. Optimal thiolation (4–5 thiol equivalents) using IgG and the above protocol resulted after 5 to 9 hours of exposure of the oxidized IgG to PDPH.

Figure 3:
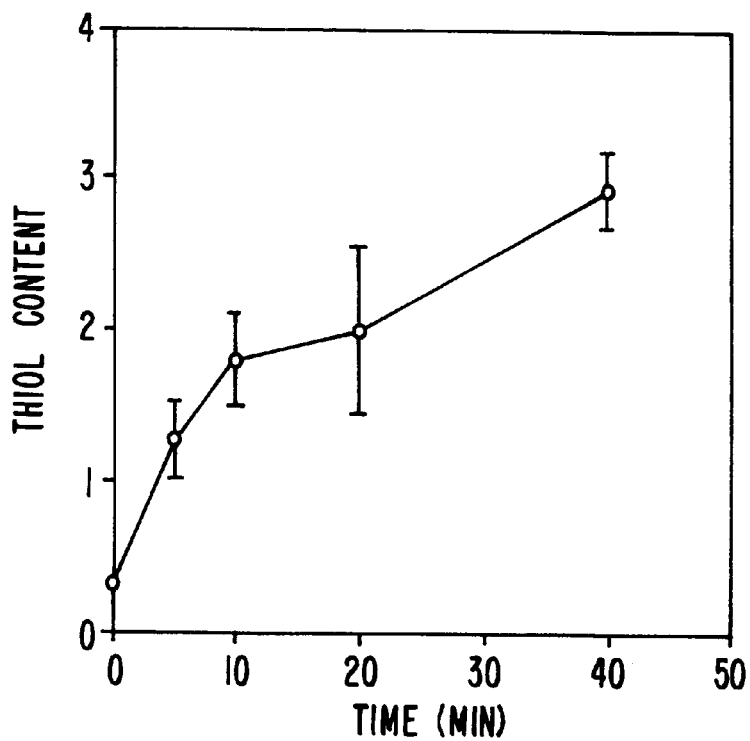
FIG. 3 is a graph showing the thiol content of the conjugate of oxidized IgG after treatment with DTT with respect to DTT incubation time.

Optimization of DTT incubation time. Damage to the intrinsic disulfide bonds of IgG under the conditions used in the protocol was determined by exposing oxidized human IgG in SAS, produced as described above, to DTT (3.86 mg/mL of IgG solution) for 0, 5, 10, 20 and 40 minutes. The reactions were stopped by passing the IgG solutions down a SEPHADEX® G-50 column in HBS and analyzing fractions with absorbances at 280 nm of greater than 0.5 using the thiol assay described above. The mean value was used for the relevant data point (see FIG. 3). At least some of the thiol functions generated under the protocol conditions (1–2 thiol equivalents) are due to DTT damage to the IgG during the deprotection step. The initial onset of the damage is rapid, suggesting that most of the DTT damage occurs while the buffer is being exchanged on the gel columns.

Figure 4:
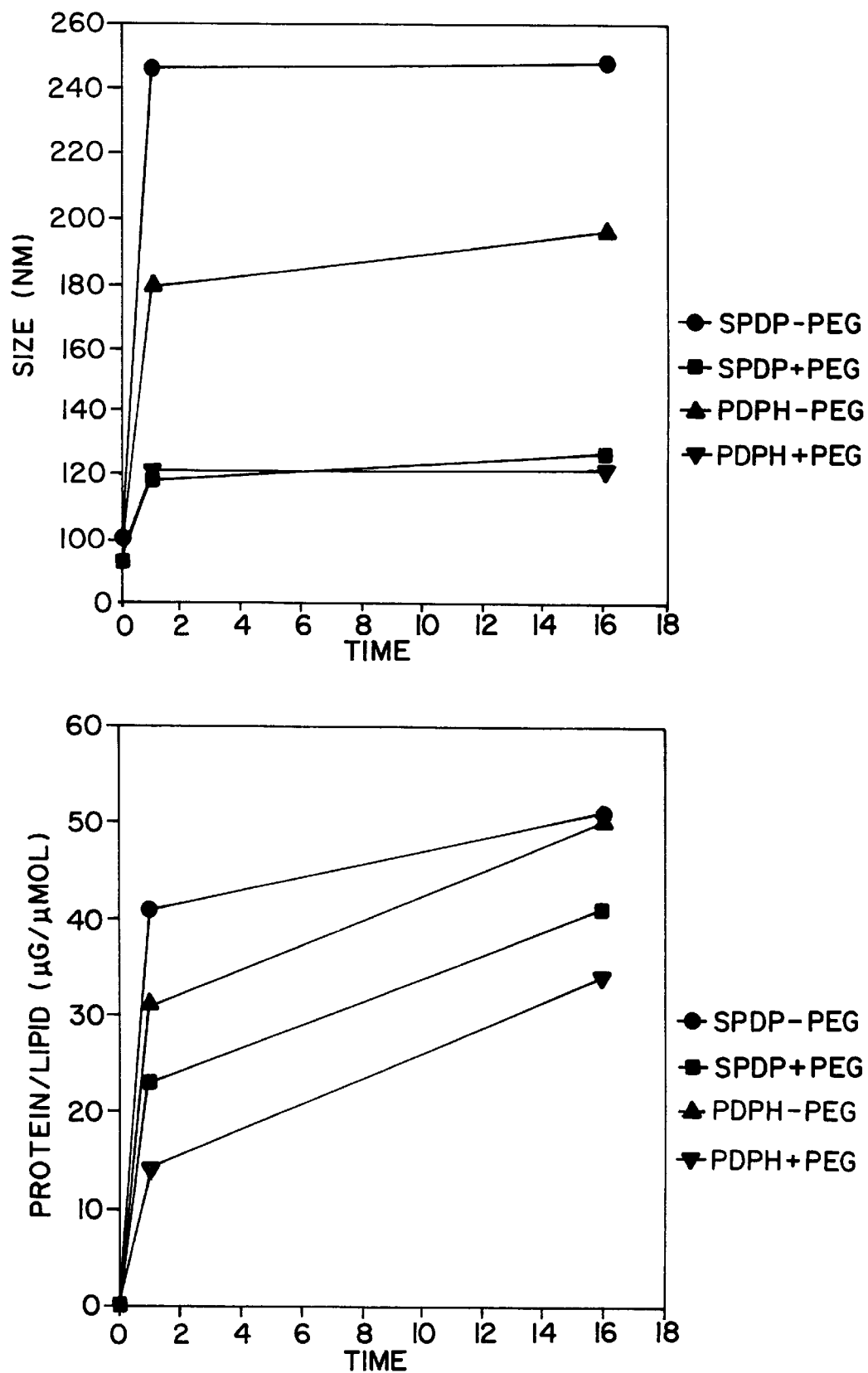
FIG. 4 is a comparison of the SPDP and PDPH protocols using an initial protein to liposome ratio of 75 µg/µmol.

Comparison of SPDP and PDPH coupling protocols. Large unilamellar vesicles were prepared in HBS from lipid mixtures comprised of 54% DSPC/ 45% cholesterol/ 1% MPB-DSPE (mole ratio) and 52% DSPC/ 45% cholesterol/ 1% MPB-DSPE/ 2% MePEGS-2000-DSPE, respectively, using the procedures described above. Two fractions of human IgG were conjugated with SPDP and PDPH, respectively, using the protocols outlined above. Aliquots of each conjugate were added to samples of each of the two liposome formulations so that the initial protein to lipid ratio was 75 µg/lmoL. The reaction mixture was then stirred at room temperature. Aliquots were removed from the reaction mixtures after 1 hour and 16 hours, and passed down a SEPHAROSE® CL4B column in HBS to remove unconjugated IgG. The recovered IgG-liposome conjugates were analyzed for lipid and protein content as described above. The size of the conjugates was determined on a Nicomp particle sizer and the result are shown in FIG. 4.

Figure 5:
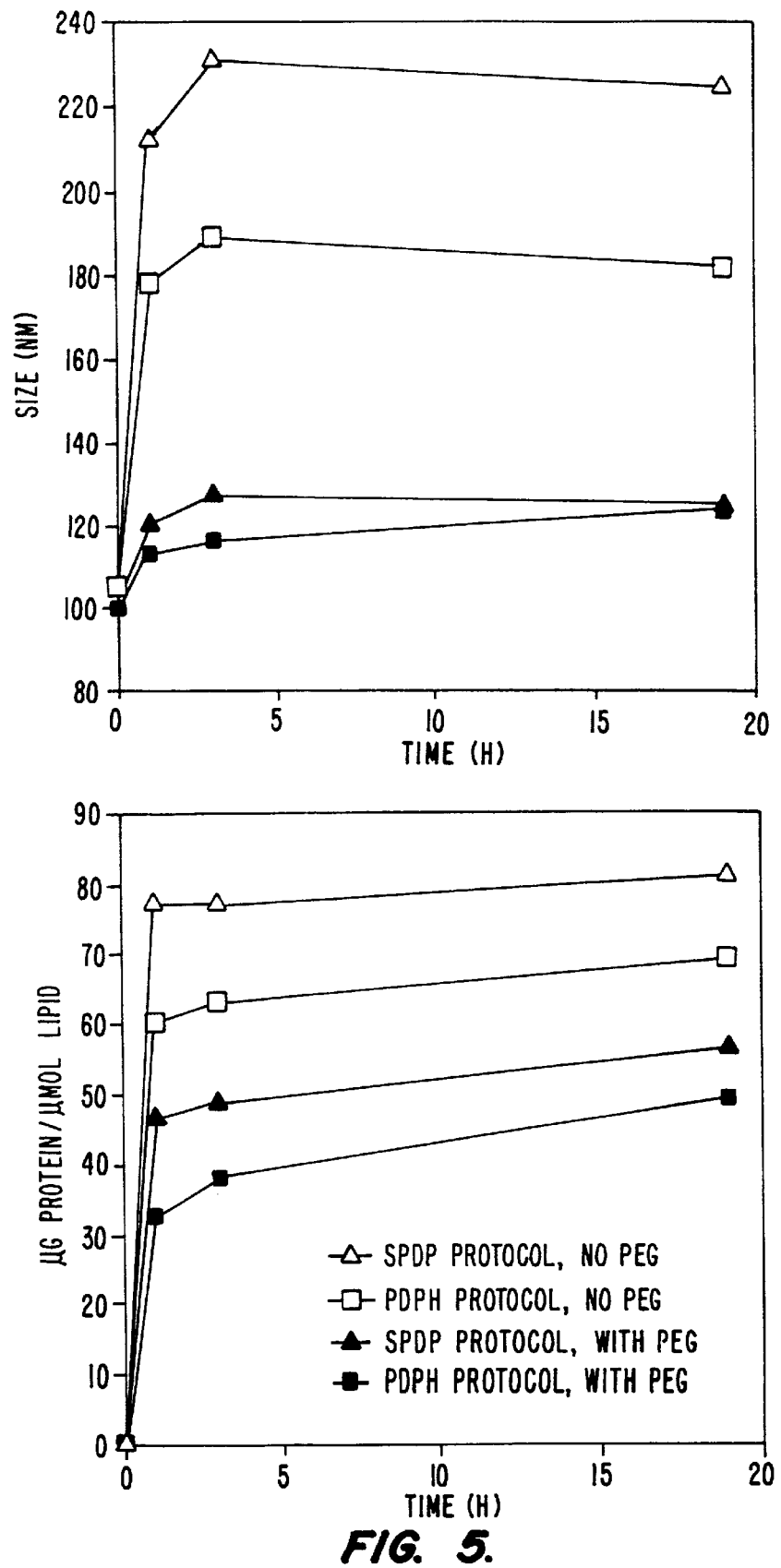
FIG. 5 is a comparison of the SPDP and PDPH protocols using an initial protein to liposome ratio of 150 µg/µmol.

The experiment was repeated using an initial protein to lipid ratio of 150 µg//µmoL, with aliquots taken from the reaction mixture at 1, 3 and 16 hours. The results are presented in FIG. 5.

The data shows that both the SPDP and PDPH protocols are effective in conjugating IgG to suitably reactive liposomes. Small differences in the levels of conjugation reflect differences in the degree of thiolation in the particular instance rather than different kinetics. The reaction is rapid in both cases, being essentially complete in 1 to 3 hours. Slightly less aggregation is observed for the PDPH protocol in the absence of MePEGS-2000-DSPE. Addition of MePEGS-2000-DSPE to the liposome composition completely inhibits aggregation. The percentage of conjugated protein is reduced for both protocols, however, the presence of PEG does not inhibit PDPH coupling relative to SPDP coupling. The use of PEG lipids in the liposome composition is important since it acts to inhibit rapid clearance of the liposomes.

EXAMPLE 2

This example provides a comparison of the in vitro binding ability of the protein-liposome conjugates having SPDP and PDPH linkages.

Figure 6:
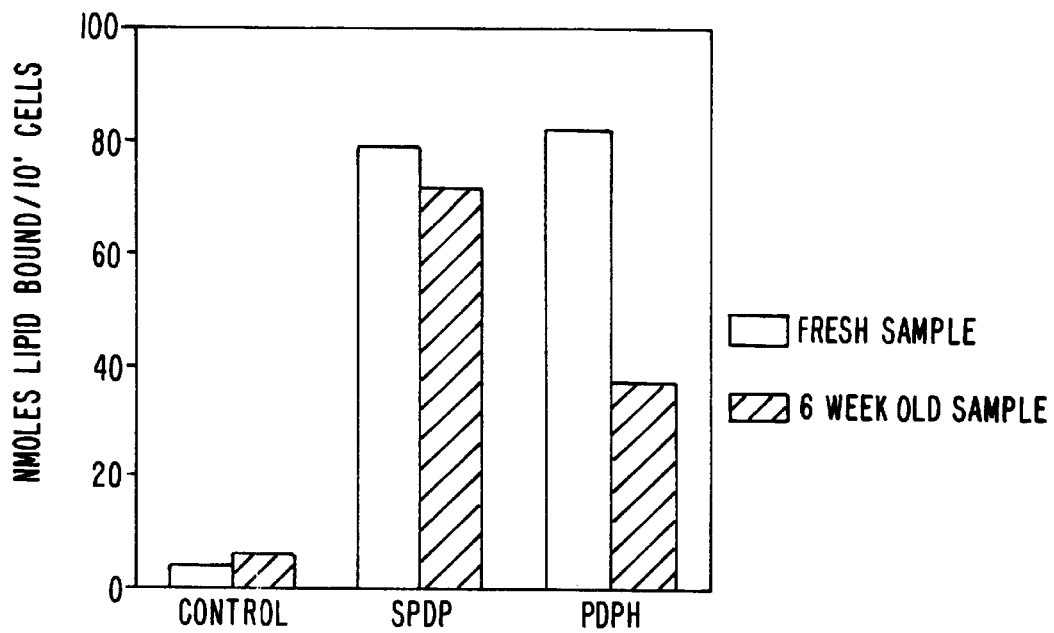
FIG. 6 shows the in vitro targeting of NRLU-10 antibody-liposome conjugates (from both the SPDP or PDPH methods) to LS-180 cells.

In vitro cell binding studies. The NRLu-10 antibody was conjugated to liposome comprised of 53% DSPC/ 45% cholesterol/ 1% MPB-DSPF/ 2% MePEGS2000-Cer (mole ratio) and a small amount of [$^3$H]-cholesterol hexadecyl ether, using the SPDP and PDPH protocols outlined in Example 1. Human colon carcinoma LS180 cells were aliquoted ($10^8$ cell/mL) into round bottomed polystyrene tubes and incubated with NRLu-10-liposome conjugates or control liposomes, at a concentration of 1 mM lipid for one hour at 37° C. with shaking. The cells were washed three times with RPM1 with 10% FBS. After the third wash the pellet was resuspended in RPM1 (500 µL) and transferred to a scintillation vial. The amount of bound lipid was determined from the tritium count. The results are presented in FIG. 6. The experiment was repeated with the same liposome conjugates after six weeks of storage at 5° C. The results indicated comparable binding behavior when using the two protocols, although there was a significant reduction in targeting when using the PDPH conjugate after six weeks of storage. The hydrazone linkage of the PDPH conjugate is unstable over long periods, but can be stabilized by reduction with sodium cyanoborohydride.

Figure 7:
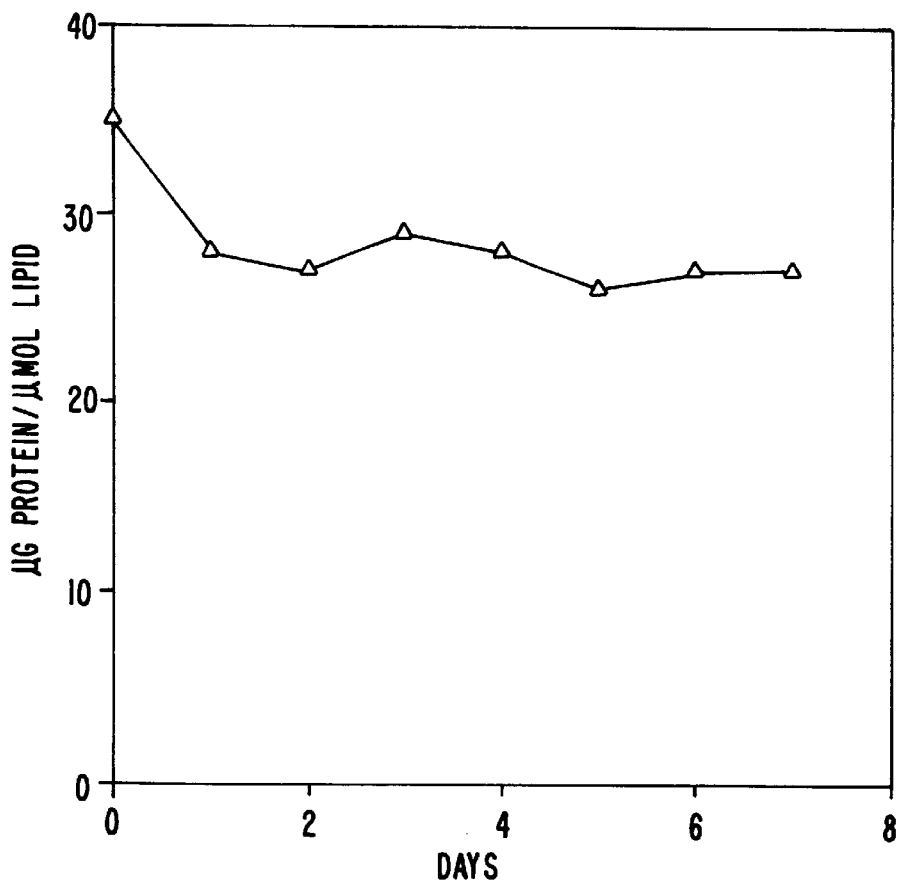
FIG. 7 shows the stability of PDPH linked human IgG-liposome conjugates in buffer at 37° C.

Stability of human IgG-liposome PDPH crosslinked conjugates at 37° C. in buffer. Human IgG was conjugated to liposomes (53% DSPC/ 45% cholesterol/ 1% MPB-DSPE/ 2% MePEGS-2000-Cer (mole ratio)) using the PDPH protocol outlined in Example 1. The conjugate was stored in a water bath at 37° C. Aliquots were removed at daily intervals and passed down a SEPHAROSE® CL4B column in HBS to remove free IgG from the liposome fraction. The samples were analyzed for lipid and protein using the procedures outlined in Example 1. The results (see FIG. 7) show that the conjugates are stable over a period of seven days.

EXAMPLE 3

This example provides a comparison for the in vivo clearance of protein-liposome conjugates having SPDP or PDPH linkages.

3.1 Preparation of Protein-Liposome Conjugates

Preparation of Liposomes. Lipid mixtures consisting of 52% DSPC/45% cholesterol/1% MPB-DSPE/2% MePEGS-2000-Cer and 52% SM/45% cholesterol/1% MPB-DSPE/ 2% MePEGS-2000-Cer were labeled with a small amount of [$^3$H] cholesteryl hexadecyl ether and used to prepare large unilamellar vesicles in HBS as described in Example 1. The NRLu-10 antibody was modified using the SPDP and PDPH protocols described in Example 1. Aliquots of the modified antibody were added to samples of the two liposome compositions such that the final protein to lipid ratio was 75 µg/µmol. Aliquots were removed from the reaction mixtures after 1 hour and after 16 hours, and passed down a SEPHAROSE® CL-4B column to remove unconjugated protein. The liposome fractions were analyzed for lipid content using the tritium label, and for protein content using the method described in Example 1.

Figure 8:
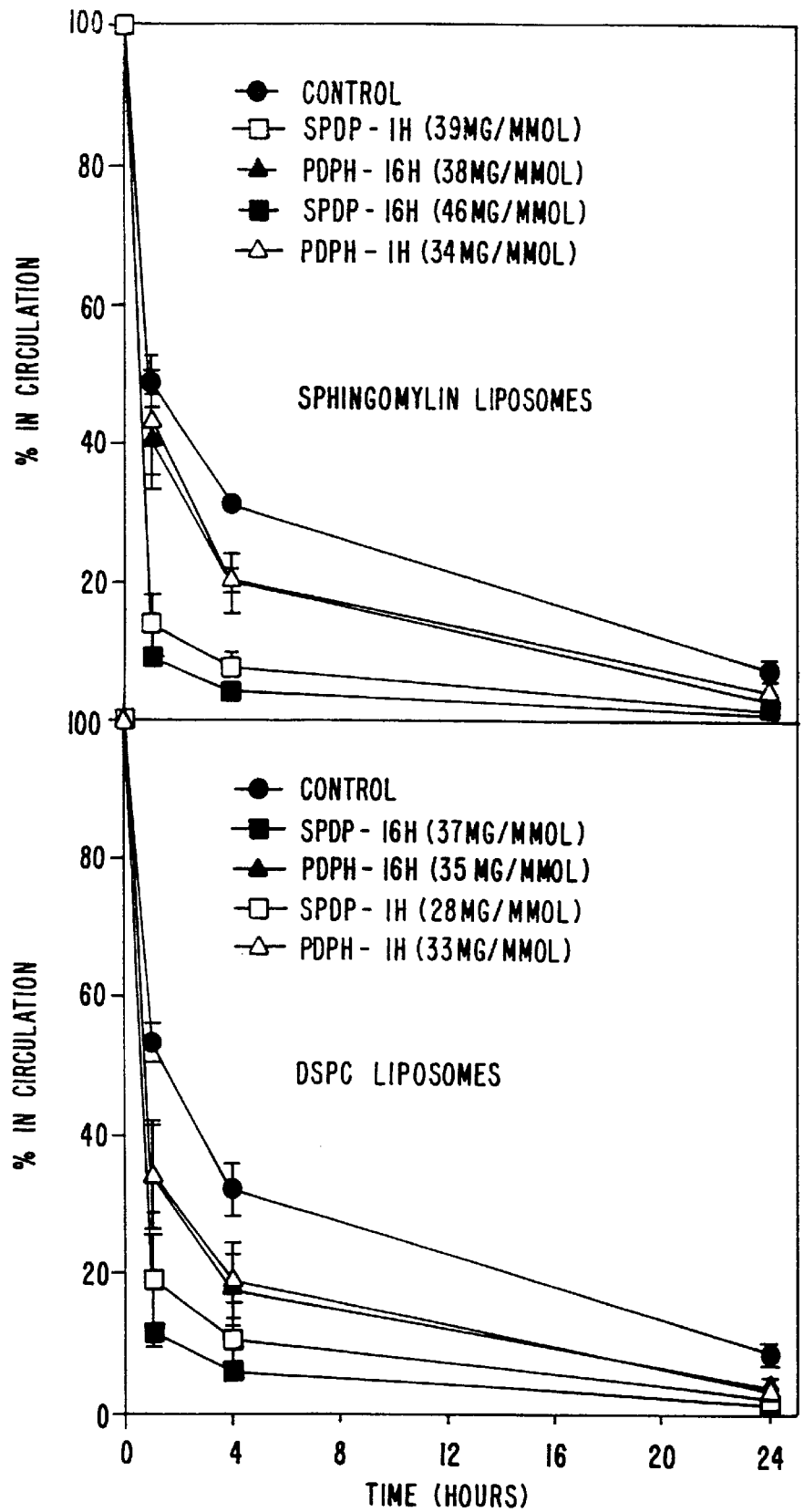
FIG. 8 is a graph showing the plasma clearance of various protein-liposome conjugates.

Groups of four CD1 mice per experimental point were given the specified treatment as a single i.v. dose via a lateral tail vein (see FIG. 8). The injection, given in a volume of 200 µL, contained a lipid dose of approximately 1 µmole lipid (25–35 µg of antibody/µmole lipid). This corresponds to a lipid dose of approximately 30 mg/kg. Liposomal lipid was measured using the lipid marker [$^3$]-cholesteryl hexadecyl ether. Previous studies have shown this lipid to be non-exchangeable and nonmetabolizable. The circulating level of injected liposomal lipid was determined at 1, 4 and 24 hours after i.v. injection. At the 1 and 4 hour time points, blood (100 µL) was obtained via retroorbital bleeding. The samples were centrifuged at 500 g for 10 min. The amount of radioactivity associated with the plasma was determined using a Beckman LS3801 scintillation counter. At 24 hours animals were asphyxiated by $CO_2$, blood was collected via cardiac puncture and placed into EDTA coated microtainers (Becton Dickenson). Plasma was prepared by centrifuging the samples at 500 g for 10 min. Lipid levels in the plasma were determined as described above where the amount of radioactivity in 50 µL of plasma was measured. The results are shown in FIG. 8. The comparison shows that liposome composition makes little difference to the clearance characteristics of the conjugates, however, the PDPH coupling protocol results in conjugates that were cleared significantly less rapidly than SPDP conjugates with comparable protein loads. Comparison of the clearance behavior of the SPDP conjugates from the 1 hour and 16 hour incubations shows that increased protein load leads to increased clearance.

Figure 9:
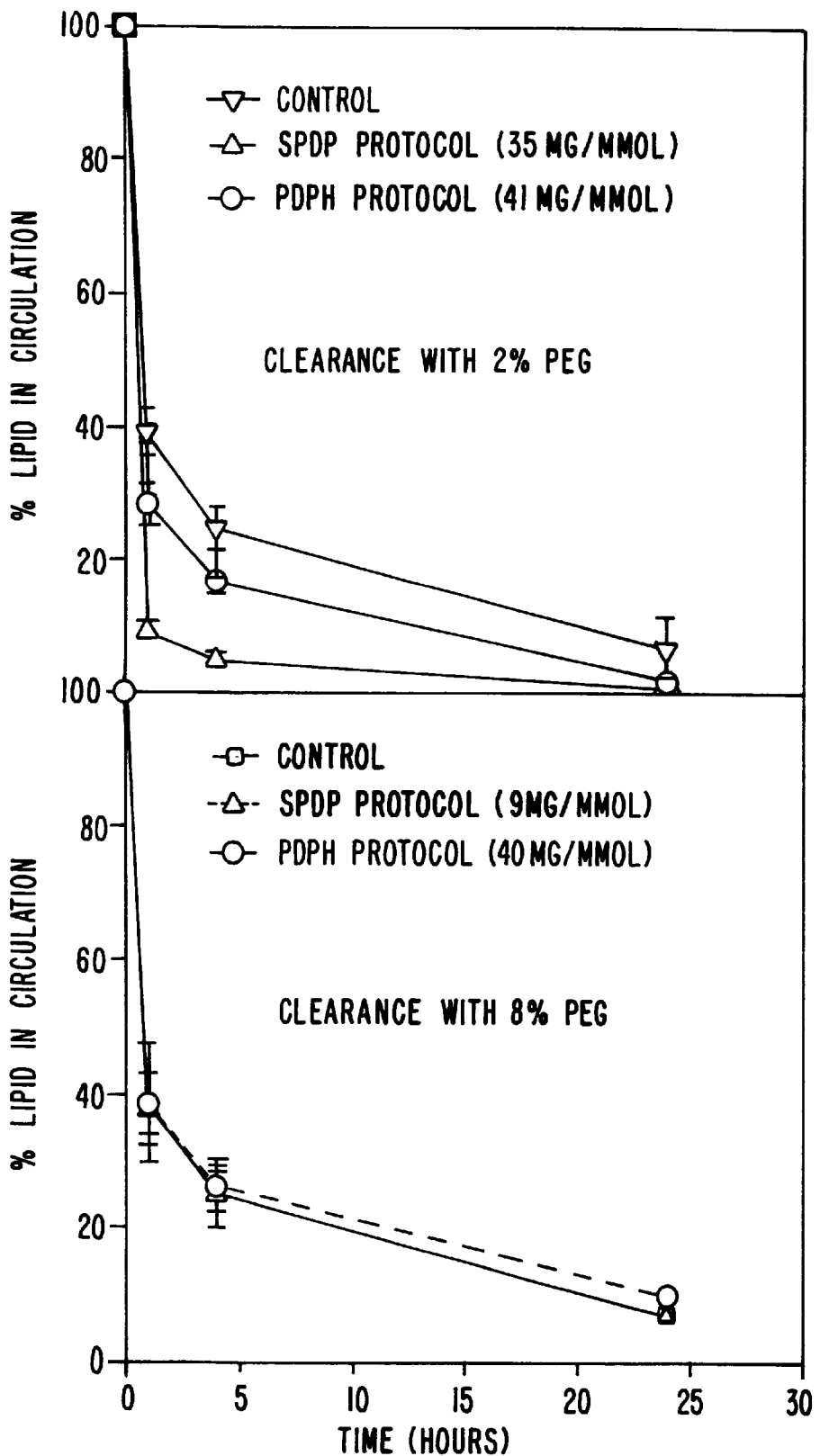
FIG. 9 is a graph showing the plasma clearance of NRLU-10-liposome conjugates having various levels of surface-bound PEG.

A second experiment was conducted using 52% DSPC/ 45% cholesterol/1% MPB-DSPE/2% MePEGS-2000-Cer and 46% DSPC/45% cholesterol/1% MPB-DSPE18% MePEGS-2000-Cer liposome compositions with the NRLu-10 antibody to determine the effect of increasing the PEG concentration on the relative performance of the PDPH and SPDP coupling protocols. A 16 hour protein-liposome (75 µg/µmol) incubation period was used in this case (see FIG. 9). Increasing the MePEGS-2000-Cer concentration to 8% severely inhibited the coupling reaction using the SPDP protocol but had little effect on the PDPH protocol. Conjugates with 8% MePEGS-2000-Cer had clearance characteristics comparable to those of the controls.

Figure 10:
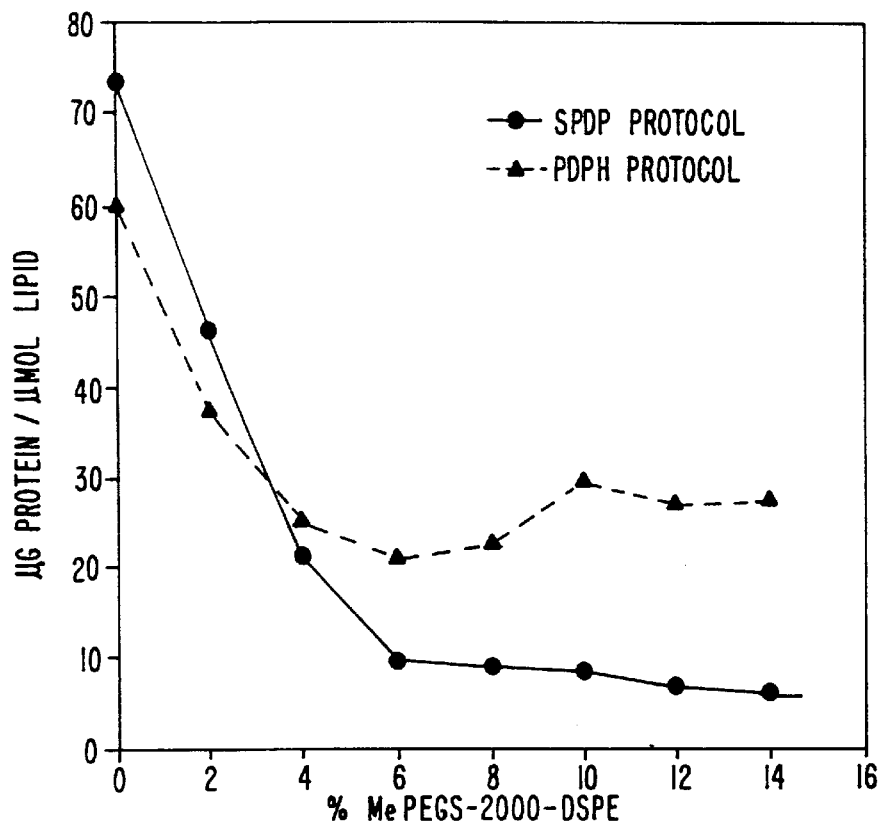
FIG. 10 shows the lipid and protein content of IgG-liposome conjugates as a function of the amount of MePEGS-2000-DSPE.

A third experiment was conducted in which human IgG was conjugated to liposomes with compositions consisting of 54-n % DSPC/ 45% cholesterol 1% MPB-DSPE/ n% MePEGS-2000-DSPE, where n=0, 2, 4, 6, 8, 10, 12 and 14, using the SPDP and PDPH coupling protocols such that the initial protein to lipid ratio was 150 μg/μmol. Liposome preparation and the conjugation reaction were carried out with standardized concentration conditions using the protocols outlined in Example 1. The reactions were stopped after 16 hours by passing the reaction mixtures down a SEPHAROSE® CL-4B column in HBS. Lipid and protein content were determined using the procedures outlined in Example 1, and the results are presented in FIG. 10. Increasing the MePEGS-2000-DSPE concentrations resulted in a rapid decrease in protein coupling efficiency until about 6%, after which the coupling efficiency appeared to stabilize. These results suggest that an optimal PEG concentration for clearance purposes lies in the range of about 4–6%.

EXAMPLE 4

This example illustrates the targeted delivery of doxorubicin to tumor cells using antibody-liposome conjugates prepared by the PDPH protein oxidation method.

4.1 Preparation of Antibody-Liposome Conjugates Having Encapsulated Doxorubicin

Preparation of Liposomes. Large unilamellar vesicles were prepared according to the methods described above. Lipid mixtures consisting of 52% DSPC/45% cholesterol/ 2% MePEGS-2000-Cer/1% MPB-DPPE (mole ratio) and a small amount of [$^3$H] cholesteryl hexadecyl ether were dissolved in chloroform. In some preparations the DSPC was substituted with SM. The solutions were subsequently concentrated under a stream of nitrogen gas to produce a homogeneous lipid film. The film was then placed under high vacuum for at least 4 hours before hydration at 65° C. with 300 mM methylammonium sulfate. The resulting lipid preparation (50 mM) was frozen and thawed 5 times prior to extrusion 10 times through three stacked 100 nm polycarbonate filters (Nuclepore) using an extrusion apparatus (Lipex Biomembranes, Inc.) set to 65° C. Liposome particle size was determined by quasielastic light scattering (QELS) measurements (using a Nicomp 370 particle sizer operating at a wavelength of 632.8 nm). The external buffer was exchanged with saline on SEPHADEX® G-25.

Doxorubicin Encapsulation. Doxorubicin was loaded into the liposomes using a 300 mM methylammonium sulfate gradient method (see, co-pending application Ser. No. 08/399,692, incorporated herein by reference).

Coupling of NRLU-10 Antibody to Liposomes. The NeoRx NRLU-10 antibody was modified with PDPH and linked through the carbohydrate coupling procedure described in Example 1.

4.2 NRLU-10 Clearance, Biodistribution and Targeting

SCID mice (RAG2) were injected with LS180 colon tumor cells into the flank of the hind leg. The tumors were grown for 10 days before intravenous injection of a liposomal formulation. Formulations consisted of doxorubicin loaded into 2% PEG liposomes, NRLU-10 antibody-liposome conjugates (from DSPC/Chol) or NRLU-10 antibody-liposome conjugates (from SM/Chol). Mice were injected with a lipid dose of 40 mg/kg which corresponded to a doxorubicin dose of 8 mg/kg. Blood was collected at 1, 4, 24, 48 and 72 hours after injection. Tumor and organ distributions were determined at 24, 48 and 72 hours. The quantitation of lipid was determined in these samples as mentioned above.

Figure 11:
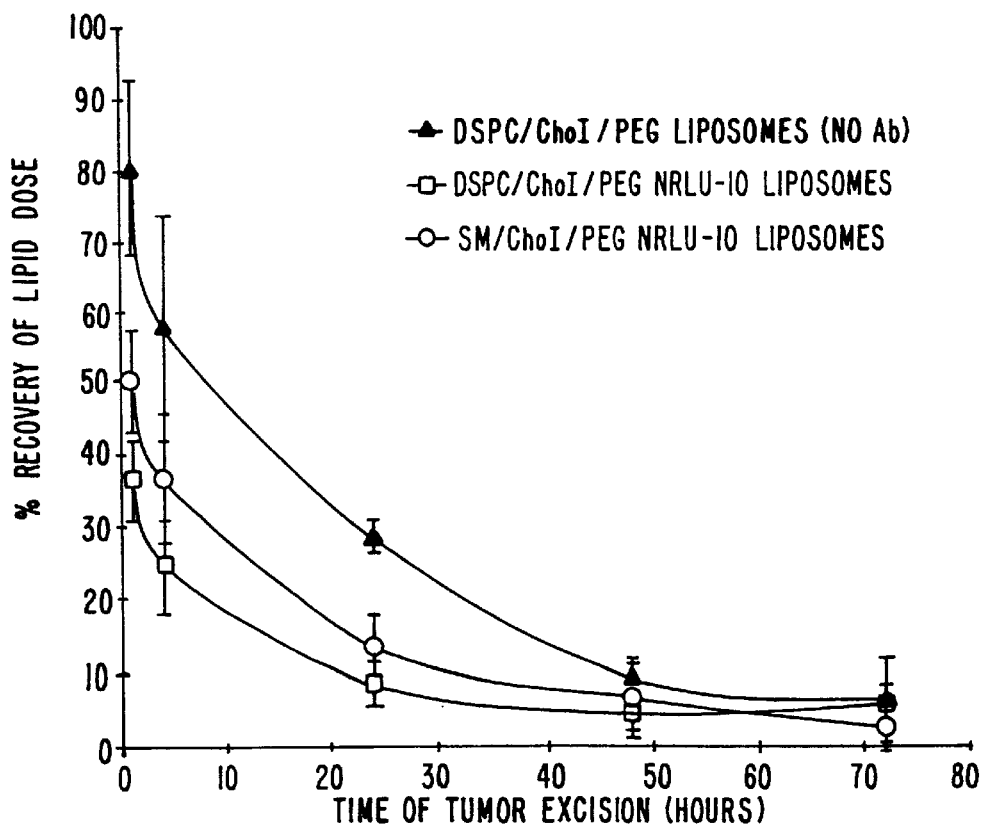
FIG. 11 is a graph showing the plasma clearance of antibody-liposome conjugates in RAG2 mice bearing LS180 tumors.

In the second group of experiments a slightly different antibody-liposome formulation was used. In this study the antibodies were linked through the carbohydrate group. The circulating levels of three different formulations of liposomal doxorubicin were determined at various time points. The results, in tumor bearing SCID mice were very similar to those previously seen in CD1 mice with approximately 50% lower circulating levels in the antibody-liposome preparations (FIG. 11). The reduced clearance of the SM system in FIG. 11 is due to a higher dose on a mole basis as the molecular weight of SM is lower than that of DSPC.

Figure 12:
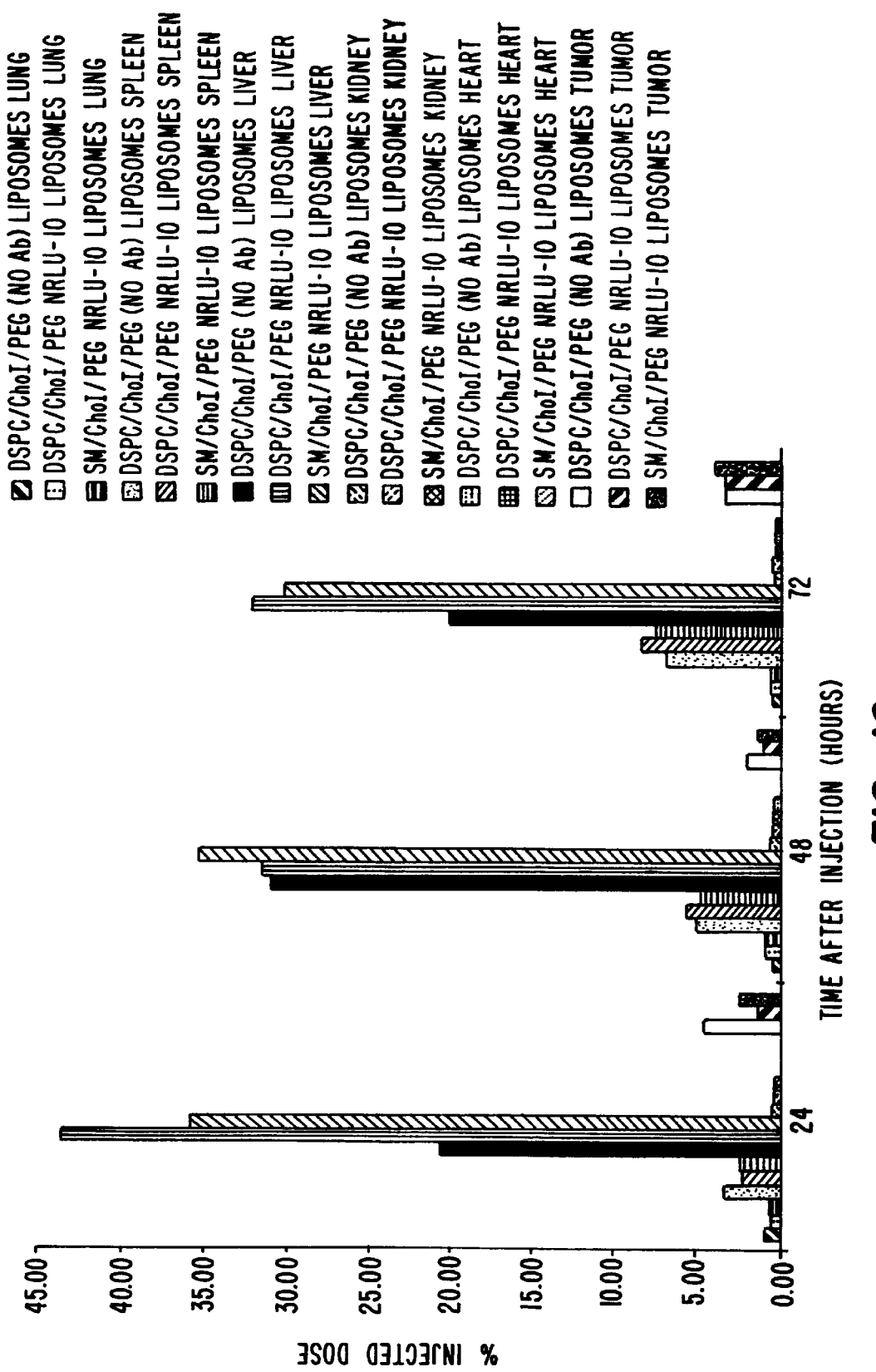
FIG. 12 is a bar graph showing the tissue biodistribution of antibody-liposome conjugates in RAG2 mice bearing LS180 tumors.

After 3 days the level of drug delivery to the tumor using the targeted systems was as high as that found with control systems. Analysis of the various tissues reveals the expected biodistribution of these systems with the majority of the dose accumulating in the liver (FIG. 12).

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. An antibody-liposome conjugate of formula I

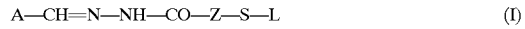

$$A-CH=N-NH-CO-Z-S-L \qquad (I)$$

wherein

A is an oxidized antibody;

L is a liposome, said liposome consisting essentially of a steric barrier molecule and a sulfhydryl-reactive lipid selected from the group consisting of N-(p-maleidophenyl)butyryl)-1,2-sn-dipalmitoylphosphatidylethanolamine, N-((6(iodoacetyl)amino)hexanoyl)-1,2-sn-dipalmitoylphosphatidylethanolamine, N-(4-(p-maleidophenyl)butyric)1,2-sn-distearoylphosphatidylethanolamne, and N((6(iodoacetyl)amino) hexanoyl)-1,2-sn-distearoylphosphatidylethanolamine;

Z is a member selected from the group consisting of a $C_1$–$C_{11}$ alkyl linking group and a $C_2$–$C_{11}$ alkenyl linking group, each of which is optionally substituted by radicals selected from the group consisting of —OH, —OR, —NH$_2$, —NHR, —NRR', —OCOR and —NHCOR, wherein R and R$^1$ are independently $C_1$–$C_5$ alkyl; and wherein the S-L linkage is a covalent attachment of the sulfhydryl moiety with said sulfhydryl-reactive lipid.

2. An antibody-liposome conjugate in accordance with claim 1, wherein Z is a $C_1$–$C_{11}$ alkyl linking group.

3. An antibody-liposome conjugate in accordance with claim 1, wherein —(CH$_2$)$_2$—.

4. An anti-body-liposome conjugate in accordance with claim 1, wherein said steric barrier molecule is a polyethyleneglycol-lipid conjugate.

* * * * *